(12) United States Patent
Oliver et al.

(10) Patent No.: US 8,685,486 B2
(45) Date of Patent: Apr. 1, 2014

(54) METHOD OF AND SYSTEM FOR APPLYING BLOCKING MATERIAL TO ASSAY SUBSTRATES

(75) Inventors: Kevin Oliver, Reading, MA (US); Toni Holway, Bedford, MA (US); Travis Sullivan, Chelmsford, MA (US)

(73) Assignee: Aushon Biosystems, Inc., Billerica, MA (US)

( * ) Notice: Subject to any disclaimer, the term of this patent is extended or adjusted under 35 U.S.C. 154(b) by 54 days.

(21) Appl. No.: 13/206,775

(22) Filed: Aug. 10, 2011

(65) Prior Publication Data

US 2012/0135154 A1    May 31, 2012

Related U.S. Application Data

(60) Provisional application No. 61/372,552, filed on Aug. 11, 2010.

(51) Int. Cl.
*B05D 3/00* (2006.01)

(52) U.S. Cl.
USPC ........... 427/2.11; 424/423; 427/2.1; 436/514; 623/1.38; 623/1.53

(58) Field of Classification Search
USPC ....... 424/423; 427/2.1, 2.13; 422/100; 435/6; 623/1.38; 436/514
See application file for complete search history.

(56) References Cited

U.S. PATENT DOCUMENTS

| | | | |
|---|---|---|---|
| 6,626,939 B1 * | 9/2003 | Burnside et al. | 623/1.38 |
| 7,455,816 B2 | 11/2008 | Steuer | |
| 2002/0064482 A1 * | 5/2002 | Tisone et al. | 422/100 |
| 2004/0058327 A1 * | 3/2004 | Pan et al. | 435/6 |
| 2005/0281857 A1 * | 12/2005 | Heyer et al. | 424/423 |
| 2006/0032747 A1 | 2/2006 | Anderson et al. | |
| 2006/0189123 A1 | 8/2006 | Saitou et al. | |
| 2007/0020711 A1 | 1/2007 | Wheat | |
| 2008/0015116 A1 | 1/2008 | Bass et al. | |
| 2008/0213481 A1 | 9/2008 | Caracci | |
| 2009/0137428 A1 | 5/2009 | Okabe | |
| 2009/0280649 A1 | 11/2009 | Mayer et al. | |
| 2010/0047845 A1 | 2/2010 | Woodside et al. | |

OTHER PUBLICATIONS

Hartmann et al., Increasing robustness and sensitivity of protein microarrays through microagitation and automation, Feb. 2006, Analytica Chimica Acta 564 (2006), pp. 66-73.*

Hartmann et al., Non-contact protein microarray fabrication using a procedure based on liquid bridge formation, Anal Bioanal Chem, 393:591-98 (2009).

(Continued)

*Primary Examiner* — Dah-Wei Yuan
*Assistant Examiner* — Andrew Bowman
(74) *Attorney, Agent, or Firm* — Wilmer Cutler Pickering Hale and Dorr LLP

(57) ABSTRACT

Methods of and systems for applying blocking material to assay substrates are disclosed. A method includes supplying an assay substrate having at least one surface. A first portion of the surface of the substrate has at least one analysis feature thereon, and a second portion of the surface of the substrate lacks analysis features. The method also includes generating a spray of a blocking material in proximity to the surface of the substrate and continuing the spray generation in proximity to the surface of the substrate at least until the second portion of the surface of the substrate is substantially covered by the blocking material.

9 Claims, 4 Drawing Sheets

(56) References Cited

OTHER PUBLICATIONS

Surmodics Protein Stability Solutions: An Overview of Products for In Vitro Applications (2005).

Hartmann et al., Increasing robustness and sensitivity of protein microarrays through microagitation and automation, Analytica Chimica Acta, 564, 66-73 (2006).

International Search Report issued for PCT/US11/47168, dated Dec. 16, 2011 (2 pages).

* cited by examiner

METHOD OF AND SYSTEM FOR APPLYING BLOCKING MATERIAL TO ASSAY SUBSTRATES

CROSS-REFERENCE TO RELATED APPLICATIONS

This application claims the benefit under 35 U.S.C. §119 (e) of U.S. Provisional Patent Application Ser. No. 61/372,552, filed on Aug. 11, 2010, entitled Method of and System for Applying Blocking Material to Assay Substrates, incorporated by reference herein in its entirety.

BACKGROUND

1. Field of Invention

The present invention relates to the preparation of assay substrates, and, more specifically, to the application of a blocking material to an assay substrate that has been printed with features.

2. Description of Related Art

An assay substrate is a surface upon which various chemical and/or biological analyses can be performed. Examples include microarray plates, glass slides, and microtiter plates. A microtiter plate is a flat plate that has multiple "wells" formed in its surface. Each well can be used as a small test tube into which various materials can be placed for the purposes of performing chemical analysis. One illustrative use of microtiter plates includes an enzyme-linked immunosorbent assay (ELISA), which is a modern medical diagnostic testing technique.

In ELISA, in general, a capture antibody is printed in the bottom of a well in a microtiter plate. The capture antibody has specificity for a particular antigen for which the assay is being performed. A sample to be analyzed is added to the well containing the capture antibody, and the capture antibody "captures" or immobilizes the antigen contained in the sample. A detect antibody is then added to the well, which also binds and/or forms a complex with the antigen. Further materials are then added to the well which cause a detectable signal to be produced by the detect antibody. For example, when light of a specific wavelength is shone upon the well, the antigen/antibody complexes will fluoresce. The amount of antigen in the sample can be inferred based on the magnitude of the fluorescence. In another example, a compound can be added to the well that causes the detect antibody to emit light within a predetermined wavelength (e.g., 400-500 nm). This light can be read by a CCD camera to measure the optical brightness of the emitted light.

BRIEF SUMMARY

In one aspect, the invention features methods of and systems for applying blocking material to assay substrates.

In another aspect, the invention features a method including supplying an assay substrate having at least one surface. A first portion of the surface of the substrate has at least one analysis feature thereon, and a second portion of the surface of the substrate lacks analysis features. The method also includes generating a spray of a blocking material in proximity to the surface of the substrate and continuing the spray generation in proximity to the surface of the substrate at least until the second portion of the surface of the substrate is substantially covered by the blocking material.

In a further aspect, the at least one analysis feature has a first surface in contact with the surface of the substrate and a second surface not in contact with the surface of the substrate. The method also optionally includes continuing the spray generation in proximity to the surface of the substrate until the second surface of the analysis feature is substantially covered by the blocking material.

In yet another aspect, the spray of the blocking material is generated by an airbrush. Optionally, the airbrush generates a spray pattern having a central axis, and the airbrush is held in relation to the substrate to maintain the central axis of the spray pattern substantially normal to the at least one surface of the substrate.

In still a further aspect, the airbrush, in operation, has a blocking material flow rate through the airbrush and an air supply pressure. The flow rate through the airbrush ranges from about 5 ml/min to about 20 ml/min, and the air supply pressure ranges from about 34 kPa to about 207 kPa.

In an aspect of the invention, the spray of the blocking material originates at a nozzle, and the surface of the substrate is within about 2 cm to about 41 cm of the nozzle.

In another aspect, the spray of the blocking material originates at a nozzle, and the method further includes moving at least one of the nozzle and the assay substrate relative to each other to distribute the blocking material over substantially the entire surface of the substrate. Optionally, the method includes disposing the assay substrate on a conveyor, a portion of the conveyor being disposed below the nozzle, and actuating the conveyor to bring the assay substrate into the spray of blocking material.

In yet another aspect, the assay substrate is a microtiter plate. The microtiter plate has a plurality of wells, and the at least one analysis feature is disposed within one of the wells. Optionally, the method also includes, adding blocking material to at least one well via a pipette.

In still a further aspect, the assay substrate is a functionalized slide.

DETAILED DESCRIPTION

Figure 1:
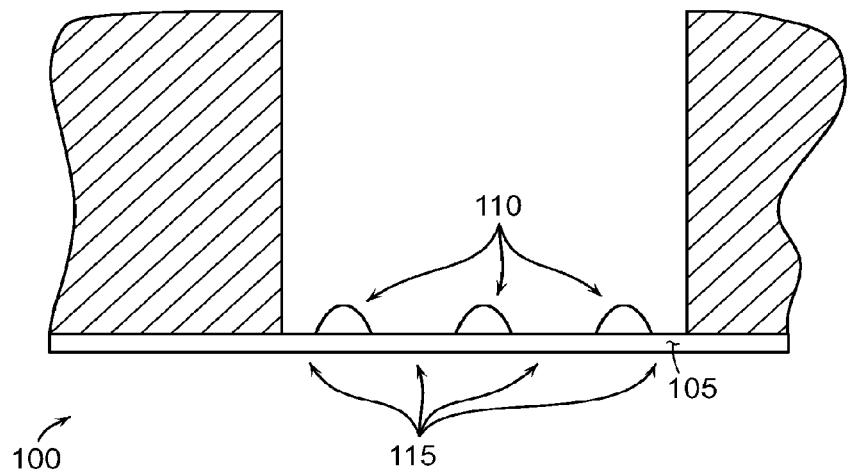
FIG. 1 shows a cross-sectional side view of a single well in a microtiter plate.

FIG. 1 shows an illustration of a cross-sectional side view of a single well in a microtiter plate 100. The bottom of the well is formed of a polystyrene base 105. During the preparation of a microtiter plate for use in an ELISA, many different capture antibody "spots" or "features" 110 are printed in the well and adhere to the polystyrene base 105. The features can be about 320-380 μm in diameter, for example. After printing the capture antibody features 110, a blocking material is added to the well to block plate binding sites 115 that remain on the plate 100. This prevents non-selective binding of sample antigens to the base of the well during the ELISA, which would give false readings.

Figures 2A, 2B, 2C:
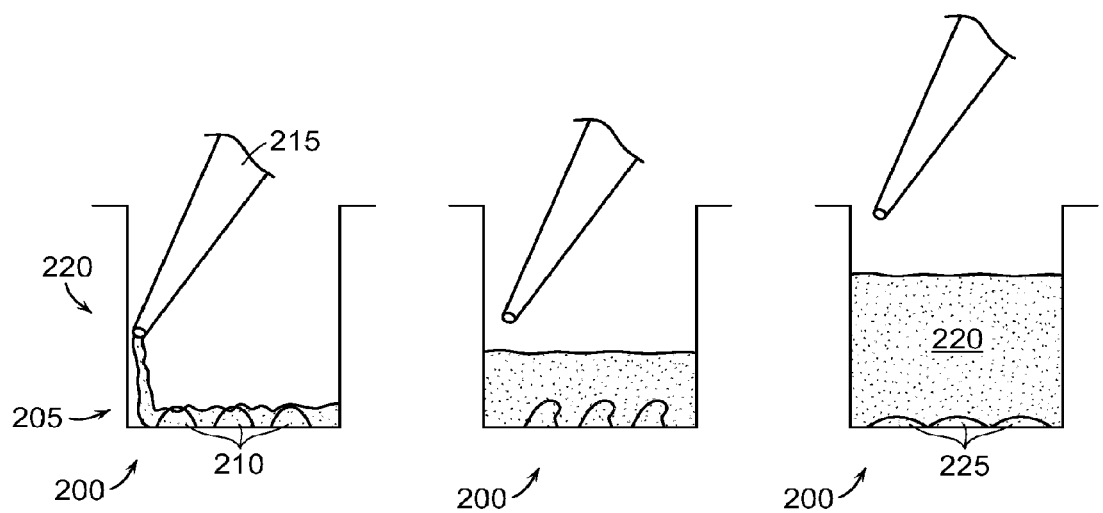
FIG. 2A-C show a series of cross-sectional side views of a well during a known method of adding a blocking material to a well.

FIGS. 2A-C show a series of cross-sectional side views 200 of a well 205 during a known method of adding a blocking material to a well during the preparation of an ELISA plate. After the features 210 have been printed, a micropipette 215 containing a solution of blocking material 220 is used to add about 200 μL of the solution to the well 205. However, this method can introduce undesirable effects inside the plate well. Specifically, applying a blocking material solution directly above one or more of the printed features 210 can destroy the shape of the feature due to the force of the blocking material solution impacting the printed feature. Thus, a typical approach is to apply the blocking solution along a portion of the wall 220 of the well 205.

Such an approach can reduce the impact force experienced by the printed features 210. However, in some cases, the printed features 210 can still be "toppled" by the incoming blocking material solution washing over the top of the printed feature (as shown in FIG. 2B). The toppled features can then form large deformed spots 225 on the surface of the bottom of the well plate (as shown in FIG. 2C).

Figure 3:
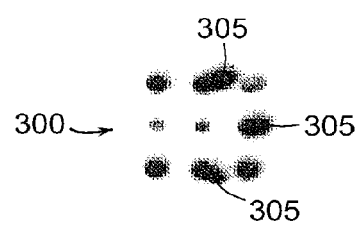
FIG. 3 shows a top view of a number of printed features after the application of a blocking material using a known method.

FIG. 3 shows a top view 300 of a number of printed features after the application of a blocking material using the known method illustrated in FIGS. 2A-2C. As shown in FIG. 2, several of the features have toppled and spread across larger portions of the bottom surface of the well plate. Thus, these features lack a clearly defined circle when viewed from above. These altered features can be more difficult to detect or "read". For example, an automated ELISA reader may misread a malformed feature, the toppled feature may interfere with an adjacent feature, and/or the intensity of the feature may be affected. Moreover, a user of a plate with malformed features may perceived the plate as lacking quality, or the user may lack confidence in the results of the analysis.

Figure 4:
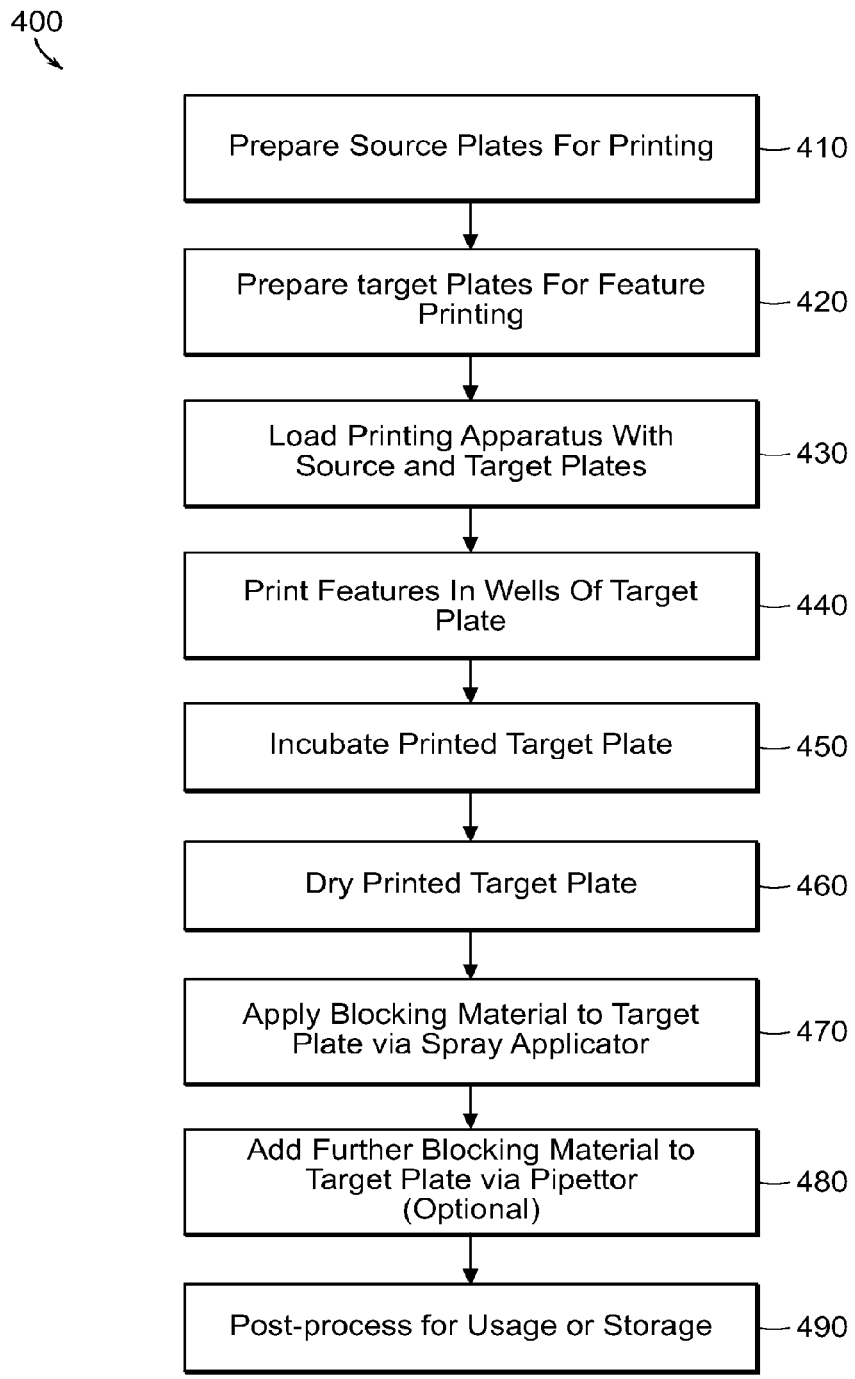
FIG. 4 shows a method of preparing a microtiter plate in accordance with some embodiments.

FIG. 4 shows a method 400 of preparing a microtiter plate in accordance with some embodiments. Method 400 reduces or eliminates malformation and/or toppling of features during the addition of blocking material to the microtiter wells. As used herein, a "target plate" is a plate that is to be prepared (e.g., printed, blocked, and processed for later usage) for a particular set of analyses. Whereas, a "source plate" is a microtiter plate that has a supply of the material to be printed onto a target plate. For example, the wells of a source plate can be filled with various types of antibodies that are to be printed onto target plates.

In accordance with method 400, the source plate is prepared for the printing process (step 410). This can include filling the wells of the source plate with the desired material to be printed onto the target plate. Next, the target plate is prepared for printing (step 420). This can include washing and/or other surface treatments to enable the material to be printed to properly adhere to the bottom surface of the plate well. The source and target plates are then fit into a printing apparatus (e.g., a 2470 Arrayer available from Aushon Biosystems, Inc. of Billerica, Mass.) (step 430). Features are printed in the wells of the target plate (step 440), the printed target plate is incubated for a period of time (step 450), and the target plate is dried (step 460).

Figures 5A, 5B, 5C:
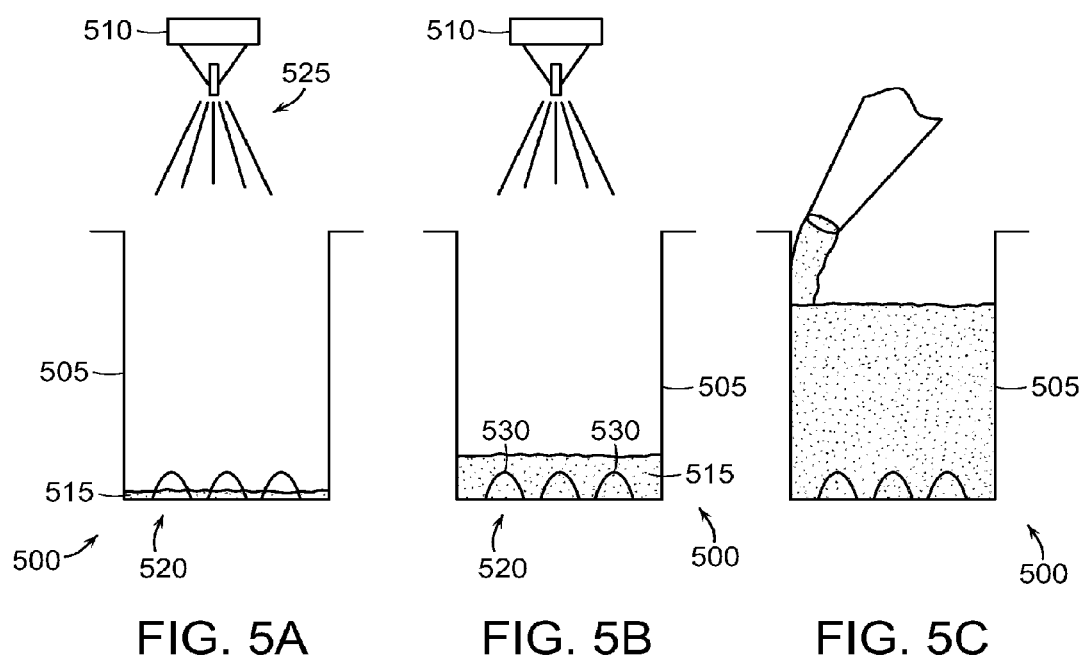
FIGS. 5A-B show a series of cross-sectional side views of a well during a method of adding a blocking material to a well in accordance with some embodiments.
FIG. 5C shows a cross-sectional side view of a well during an optional step of a method of adding a blocking material to the well in accordance with some embodiments.

Next, a blocking material is applied to the target plate via a spraying process (step 470). FIGS. 5A-B show a series of cross-sectional side views 500 of a well 505 during the spraying step in accordance with one implementation. In the implementation shown, an airbrush 510 (e.g., a Paasche Talon model TG0210) is used to apply the blocking material 515 to the bottom surface of the well 520 of the plate. During the spraying step, approximately 10 ml of a blocking material solution is sprayed over the entire surface of the plate. The blocking material is propelled by a compressed air source, e.g., a standard air compressor that supplies clean and dry air, at a pressure of about 138 kPa (20 psig). The flow rate of the airbrush is set to about 10 ml/min.

The nozzle of the airbrush is positioned about 15 cm (6 inches) from the surface of the plate, and the airbrush is swept across the entire surface while keeping the nozzle perpendicular to the surface of the plate. In other words, the center of the spray pattern 525 is essentially normal to the surface of the plate. The spraying is continued at least until the parts of the surface of the plate without printed features thereon is substantially covered in blocking material. Optionally, the spraying is continued at least until the level of blocking material in the well covers the printed features 530. After that level of blocking material is achieved, additional blocking material can be added by continuing the spraying process, or, optionally, additional blocking material can be added via micropipette, as described above (step 480). FIG. 5C shows a cross-sectional side view of the well during this optional step of adding blocking material to the well via pipette.

Figure 6:
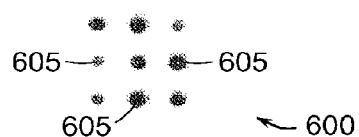
FIG. 6 shows a top view of a number of printed features after the application of a blocking material in accordance with some embodiments.

The target plate is then processed for usage or storage using known methods (step 490). For example, the target plate can be incubated at about 4° C. overnight. Alternatively, excess blocking material (e.g., the blocking material that has not bound to the bottom of the well) can be removed from the target plate, the plate can then be dried, and then the plate can be placed into a moisture-resistance package for storage. The disclosed method of applying the blocking material reduces or eliminates malformation and/or toppling of features during the addition of blocking material to the microtiter wells. FIG. 6 shows a top view 600 of a number of printed features 605 after the application of a blocking material in accordance with some embodiments. As shown in the figure, the printed features 605 have well-defined circular borders and do not have the misshapen features that appear in the plate prepared according to the known methods. Thus, plates prepared according to the methods disclosed herein have superior feature uniformity.

The scope of the invention is not limited to applications involving microtiter plates having wells therein. In another embodiment of the invention, the techniques described herein are applicable to functionalized slides (e.g., functionalized glass slides). In such an implementation, the functionalized slides lack the wells found in microtiter plates. Instead, the functionalized slide contains surface portions that have been modified by binding various compounds to the surface portions. For example, a surface of a functionalized slide can have portions to which a long-chain polymer, having certain functional groups, has been covalently linked. The functional groups enable biomolecules to be captured by the functionalized slide. When applied to a functionalized slide, the techniques herein permit portions of the slide (e.g., those parts that have not been functionalized) to be blocked while reducing disruption to the functionalized areas of the slide.

The application of the blocking material as described herein can be applied by-hand. In some implementations, the blocking can be applied by automated machinery. For example, after printing, incubating, and drying (steps 440, 450, and 460), the plate can be placed on a conveyor over which is mounted one or more spray nozzles. The rate of the conveyor is controlled to ensure adequate residence time of the plates within the spray pattern 525 of the one or more nozzles. For example, if the total flow rate of all of the nozzles is about 10 ml/min, the conveyor speed can be controlled to provide that at least some portion of the surface of the plate is under the spray pattern for 1 minute. In another illustrative implementation, the plate can be held is a fixed position and an automated arm can direct one or more spray nozzles above the surface of the plate.

The specific operational parameters provided above are merely illustrative, and other values are within the scope of the invention. For example, the blocking material flow rate can vary between 5-20 ml/min, the distance between the airbrush flow nozzle and the surface of the plate can vary between 2-41 cm (1-16 inches), and the air pressure can vary between 34-207 kPa (5-30 psig). It is understood that these ranges are merely illustrative and are not intended to be limiting.

Figure 7A:
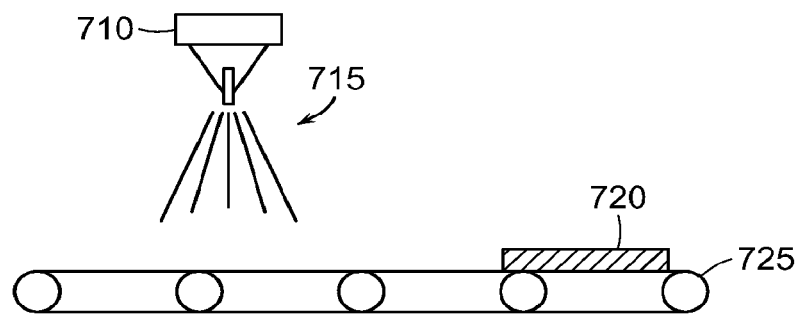
FIGS. 7A-B show a series of cross-section sides views of an assay substrate on a conveyor passing under a spray of blocking material.
Figure 7B:
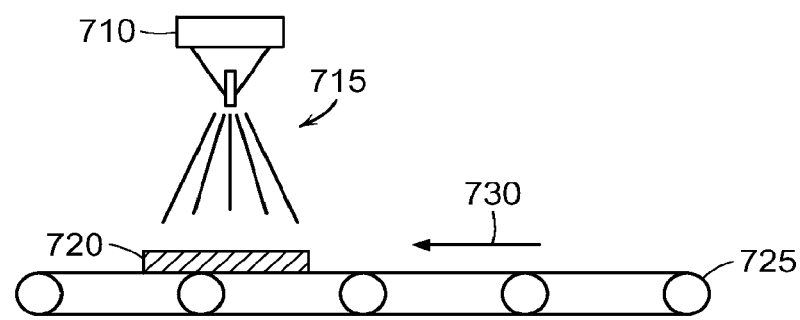

FIGS. 7A-B show a series of cross-section side views of an assay substrate on a conveyor passing under a spray of blocking material. In the implementation shown, an spray nozzle 710 is used to apply the blocking material 715 to the surface of an assay substrate 720 (e.g., a microtiter plate or a functionalized slide). The assay substrate 720 is placed on a conveyor 725, and the conveyor is actuated in the direction shown by arrow 730 to move the assay substrate 720 under the spray of blocking material 715. Although not shown, a series of assay substrates can be loaded on to conveyor in series.

The spray nozzle 710 can be a spray nozzle of an airbrush, as described in more detail above. In addition, the spray nozzle 710 can be stationary, or the spray nozzle 710 can be moved side-to-side (relative to the direction of travel of the substrate 730) so as to provide even coverage of blocking material 715 over the entire surface of the assay substrate 720.

The terms and expressions that are employed herein are terms of description and not of limitation. There is no intention in the use of such terms and expressions of excluding the equivalents of the feature shown or described, or portions thereof, it being recognized that various modifications are possible within the scope of the invention as claimed.

What is claimed is:

1. A method comprising:
   supplying an assay substrate having at least one surface, a first portion of the surface of the substrate having at least one analysis feature thereon, and a second portion of the surface of the substrate lacking analysis features;
   generating a spray of a blocking material in proximity to the surface of the substrate;
   continuing the spray generation in proximity to the surface of the substrate at least until the second portion of the surface of the substrate is substantially covered by the blocking material; and
   adding blocking material to the at least one surface of the substrate via a pipette.

2. The method of claim 1, the spray of the blocking material being generated by an airbrush.

3. The method of claim 2, the airbrush generating a spray pattern having a central axis, and the airbrush being held in relation to the substrate to maintain the central axis of the spray pattern substantially normal to the at least one surface of the substrate.

4. The method of claim 2, the airbrush, in operation, having a blocking material flow rate through the airbrush and an air supply pressure, the flow rate through the airbrush ranging from about 5 ml/min to about 20 ml/min, and the air supply pressure ranging from about 34 kPa to about 207 kPa.

5. The method of claim 1, the spray of the blocking material originating at a nozzle, the surface of the substrate being within about 2 cm to about 41 cm of the nozzle.

6. The method of claim 1, the spray of the blocking material originating at a nozzle, the method further comprising moving at least one of the nozzle and the assay substrate relative to each other to distribute the blocking material over substantially the entire surface of the substrate.

7. The method of claim 6, further comprising:
   disposing the assay substrate on a conveyor, a portion of the conveyor being disposed below the nozzle; and
   actuating the conveyor to bring the assay substrate into the spray of blocking material.

8. The method of claim 1, the assay substrate being a microtiter plate, the microtiter plate having a plurality of wells, and the at least one analysis feature being disposed within one of the wells.

9. The method of claim 8, wherein the blocking material is added to the wall of the well.

\* \* \* \* \*